United States Patent
Phythyon

(10) Patent No.: US 7,918,227 B1
(45) Date of Patent: Apr. 5, 2011

(54) ENDOTRACHEAL TUBE

(76) Inventor: Eve K. Phythyon, Twinsburg, OH (US)

( * ) Notice: Subject to any disclaimer, the term of this patent is extended or adjusted under 35 U.S.C. 154(b) by 477 days.

(21) Appl. No.: 11/190,407

(22) Filed: Jul. 28, 2005

(51) Int. Cl.
*A61M 16/04* (2006.01)

(52) U.S. Cl. ......... 128/207.18; 128/204.18; 128/207.14; 128/207.15

(58) Field of Classification Search ............ 128/207.15, 128/204.18, 207.18, 207.14
See application file for complete search history.

(56) References Cited

U.S. PATENT DOCUMENTS

| | | | |
|---|---|---|---|
| 3,599,642 A * | 8/1971 | Tindel | 128/207.14 |
| 3,948,274 A * | 4/1976 | Zeldman et al. | 128/207.14 |
| 4,050,466 A * | 9/1977 | Koerbacher | 128/207.14 |
| 4,150,676 A * | 4/1979 | Jackson | 128/207.18 |
| 4,244,362 A * | 1/1981 | Anderson | 128/207.14 |
| 4,378,796 A * | 4/1983 | Milhaud | 128/207.15 |
| 4,498,473 A * | 2/1985 | Gereg | 128/207.15 |
| 4,593,690 A * | 6/1986 | Sheridan et al. | 128/207.15 |
| 4,622,965 A * | 11/1986 | Teeple | 128/207.14 |
| 4,737,153 A * | 4/1988 | Shimamura et al. | 604/526 |
| 4,867,154 A * | 9/1989 | Potter et al. | 128/207.17 |
| 4,987,895 A | 1/1991 | Heimlich | |
| 5,024,220 A * | 6/1991 | Holmgreen et al. | 128/207.18 |
| 5,027,812 A * | 7/1991 | Shapiro et al. | 128/207.18 |
| 5,045,071 A * | 9/1991 | McCormick et al. | 604/529 |
| 5,147,370 A | 9/1992 | McNamara et al. | |
| 5,176,660 A | 1/1993 | Truckai | |
| 5,333,608 A * | 8/1994 | Cummins | 128/207.14 |
| 5,353,787 A | 10/1994 | Price | |
| 5,386,826 A * | 2/1995 | Inglis et al. | 128/207.14 |
| 5,429,127 A | 7/1995 | Kolobow | |
| 5,466,222 A * | 11/1995 | Ressemann et al. | 604/103.09 |
| 5,643,174 A * | 7/1997 | Yamamoto et al. | 600/114 |
| 5,702,374 A | 12/1997 | Johnson | |
| 5,819,723 A * | 10/1998 | Joseph | 128/207.14 |
| 5,827,242 A * | 10/1998 | Follmer et al. | 604/526 |
| 5,846,199 A * | 12/1998 | Hijlkema et al. | 600/435 |
| 5,853,004 A | 12/1998 | Goodman | |
| 6,148,818 A * | 11/2000 | Pagan | 128/207.15 |
| 6,321,749 B1 * | 11/2001 | Toti et al. | 128/207.15 |
| 6,536,437 B1 * | 3/2003 | Dragisic | 128/207.18 |
| 6,745,773 B1 | 6/2004 | Gobel | |
| 6,877,512 B2 * | 4/2005 | Imai et al. | 128/207.15 |
| 2005/0133037 A1 * | 6/2005 | Russell | 128/207.15 |

* cited by examiner

*Primary Examiner* — Edward Look
*Assistant Examiner* — Clinton Ostrup
(74) *Attorney, Agent, or Firm* — John D. Gugliotta, Esq.

(57) ABSTRACT

An improved endotracheal tube is provided which is adapted to optimally and safely accommodate the nasopharyngeal airway during nasopharyngeal intubation. The endotracheal tube includes a body having a nasopharyngeal section adapted to sealably enclose and contain a spirally-wound coil longitudinally therealong. The nasopharyngeal section integrally transposes into a rigid section which extends longitudinally from the nasopharyngeal section and terminates at a lower end of endotracheal tube. The nasopharyngeal section with incorporated spirally-wound coil allows for multiple positioning of nasopharyngeal section about a face of a patient, thereby minimizing pressure sores, abrasions, and ulcerations, and further allows for quick, easy, and efficient surgical access to the nasopharyngeal airway without requiring removal of the endotracheal tube.

17 Claims, 4 Drawing Sheets

ENDOTRACHEAL TUBE

RELATED APPLICATIONS

The present invention was first described in Disclosure Document Request 574,691 submitted for Registration on Apr. 11, 2005 under 35 U.S.C. §122, 37 C.F.R. §1.14, and MPEP §1706. There are no previously filed, nor currently any co-pending applications, anywhere in the world.

BACKGROUND OF THE INVENTION

1. Field of the Invention

The present invention relates generally to endotracheal tubes and, more particularly, to an improved endotracheal tube adapted to optimally and safely accommodate the nasopharyngeal airway during nasal airway intubation and administration of oxygen and other necessary anesthetic gaseous agents.

2. Description of the Related Art

Endotracheal tubes are used to provide access to the upper airways for controlled ventilation, assisted ventilation, and as a conduit for anesthetic gases during surgical operations, in addition to postoperative airway management.

A particular problem associated with present endotracheal tubes stems from long term intubation. Endotracheal tubes are generally of a rigid configuration and at times may be required to be fixed in place over a significant period of time, i.e., for more than seven days of intubation, thereby causing severe complications. Typical complications associated with prolonged, fixed intubation include chronic laryngotracheal stenosis, pressure sores, formation of fistulae between the trachea and the esophagus, abrasions, ulcerations, and erosion of the anterior trachea and the innominate artery. The aforementioned conditions necessitate a medical remedial action which includes but is not limited to tubular removal and subsequent corrective surgery.

Accordingly, a need has arisen for an improved endotracheal tube having a flexible, nasopharyngeal section incorporated with a spirally-wound coil which facilitates multiple positioning of the nasopharyngeal section about a face of a patient, thereby minimizing the risk of pressure sores, abrasions, and ulcerations, and which further allows for surgical access to the nasopharyngeal airway without requiring removal of the endotracheal tube in a manner which is quick, easy, and efficient. The development of the improved endotracheal tube fulfills this need.

A search of the prior art did not disclose any patents that read directly on the claims of the instant invention; however, the following references were considered related.

The following patents disclose various endotracheal tubes:
U.S. Pat. No. 6,745,773 B1, issued in the name of Gobel;
U.S. Pat. No. 5,353,787, issued in the name of Price;
U.S. Pat. No. 5,429,127, issued in the name of Kolobow; and
U.S. Pat. No. 4,987,895, issued in the name of Heimlich.

U.S. Pat. No. 5,176,660, issued in the name of Truckai discloses a flexible catheter comprised of at least one resilient, tubular layer in telescoping relation with a tubular sheath made of helically disposed crossing strands.

U.S. Pat. No. 5,147,370, issued in the name of McNamara et al. discloses a coil stent constructed from nitinol alloy, wherein the stent has ends designed to interact with a placement device specifically fabricated to retain the stent in a second smaller diameter while stent is manipulated to its desired position in the patient's body.

U.S. Pat. No. 5,853,004, issued in the name of Goodman discloses an artificial breathing device designed to be placed in the pharynx of a patient to permit or to assist the patient in the basic function of breathing.

U.S. Pat. No. 5,702,374, issued in the name of Johnson discloses an improved male luer connector assembly devised to provide and maintain a secure fluid/tight fit.

Consequently, a need has been felt for an endotracheal tube being sufficiently flexible and pliable so as to allow for multiple positioning of the upper portion of the tube about a face of a patient, thereby minimizing pressure sores, abrasions, and ulcerations, and which simultaneously allows for surgical access to the nasopharyngeal airway without requiring removal of the endotracheal tube in a manner which is quick, easy, and efficient.

SUMMARY OF THE INVENTION

Therefore, it is an object of the present invention to provide an endotracheal tube adapted to optimally and safely accommodate the nasopharyngeal airway during nasopharyngeal intubation.

It is another object of the present invention to provide an endotracheal tube constructed of a sufficiently flexible, latex-free transparent material adapted to flexibly and safely accommodate anatomically the nasopharyngeal airway.

It is another object of the present invention to provide an inflation tube which joins the body of endotracheal tube, wherein inflation tube functions as a conduit for introducing air or fluid at high or low pressure to inflate a cuff at the caudal end of endotracheal tube.

It is another object of the present invention to provide a nasopharyngeal section defined as a thin-wall section constructed of a flexible, transparent material adapted to flexibly and safely accommodate the anatomy of the nasopharyngeal airway, and further being sufficiently pliable so as to be compressed or collapsed and adapted to resume its original shape.

It is another object of the present invention to provide a nasopharyngeal section adapted to sealably enclose and contain a spirally-wound coil longitudinally therealong.

It is another object of the present invention to provide a spirally-wound coil fabricated of a shape-memory, flexible material adapted to return to or recover its original shape if compressed.

It is another object of the present invention to provide a nasopharyngeal section which integrally transposes into a rigid section which extends longitudinally therefrom and terminates at the caudal end of endotracheal tube.

It is another object of the present invention to provide an endotracheal tube having a nasopharyngeal section incorporated with a spirally-wound coil which facilitates multiple positioning of nasopharyngeal section about a face of a patient, thereby minimizing pressure sores, abrasions, and ulcerations.

It is another object of the present invention to provide an endotracheal tube having a nasopharyngeal section incorporated with a spirally-wound coil which allows for quick, easy, and efficient surgical access to the nasopharyngeal airway without requiring removal of the endotracheal tube.

It is still another object of the present invention to provide a cephalic end of endotracheal tube which is provided with an outer end fixture having an open end for providing passage into endotracheal tube.

It is yet another object of the present invention to provide a "Murphy Eye" opening defined through an outer sidewall of endotracheal tube being proximal to the caudal end thereof.

It is still another object of the present invention to provide a plurality of indicia disposed on an outer surface of endotracheal tube.

Briefly described according to one embodiment of the present invention, an improved endotracheal tube adapted to optimally and safely accommodate the nasopharyngeal airway during intubation is disclosed. The improved endotracheal tube comprises an elongated body having a cephalic end opposing a caudal end. The endotracheal tube is constructed of a sufficiently flexible, latex-free transparent material adapted to flexibly accommodate anatomically the nasopharyngeal airway.

An inflation tube joins body, wherein inflation tube functions as a conduit for introducing air or fluid at either high or low pressures to inflate a cuff at the caudal end of endotracheal tube.

The endotracheal tube further comprises a nasopharyngeal section defined as a thin-wall section constructed of a flexible, latex-free transparent material adapted to flexibly accommodate the anatomy of the nasopharyngeal airway, and further being sufficiently pliable so as to be compressed and adapted to resume its original shape. It is envisioned that the nasopharyngeal section is formed of a flexible plastic, latex-free polymer. The nasopharyngeal section is further adapted to sealably enclose and contain a spirally-wound coil longitudinally therealong.

The spirally-wound coil is fabricated of a shape-memory, flexible material adapted to return to or recover its original shape if compressed. The spirally-wound coil is constructed of a flexible material adapted to flexibly accommodate the anatomy of the nasopharyngeal airway. The spirally-wound coil is envisioned to be formed of a flexible, pliable plastic polymer.

The thin-wall section or nasopharyngeal section integrally transposes into a rigid section which extends longitudinally therefrom and terminates at the caudal end. The caudal end defines an opening adapted to allow for flow of air or gas therethrough. The rigid section is formed of a flexibly-rigid, latex-free material adapted to facilitate intubation through both the nasopharyngeal and oral airways without impedance or undue hindrance. It is envisioned that rigid section is constructed of a semi-rigid or rigid polymeric, latex-free plastic material.

The cephalic end of endotracheal tube is provided with an outer end fixture having an open end for providing air or gas passage into endotracheal tube.

An auxiliary opening or "Murphy Eye" opening is defined through an outer sidewall of endotracheal tube being proximal to the caudal end thereof. The auxiliary opening is adapted to provide an alternate ventilation port should the caudal end of endotracheal tube becomes occluded.

A plurality of indicia is provided on an outer surface of endotracheal tube. The plurality of indicia is comprised of markings which reflect length measures corresponding to endotracheal tube's length. The plurality of indicia is further comprised of a radio opaque marking to allow for x-ray evaluation.

The use of the present invention minimizes pressure sores, abrasions, and ulcerations, and further allows for surgical access to the nasopharyngeal airway without requiring removal of the endotracheal tube in a manner which is quick, easy, and efficient.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENT

1. Detailed Description of the Figures

Figure 1:
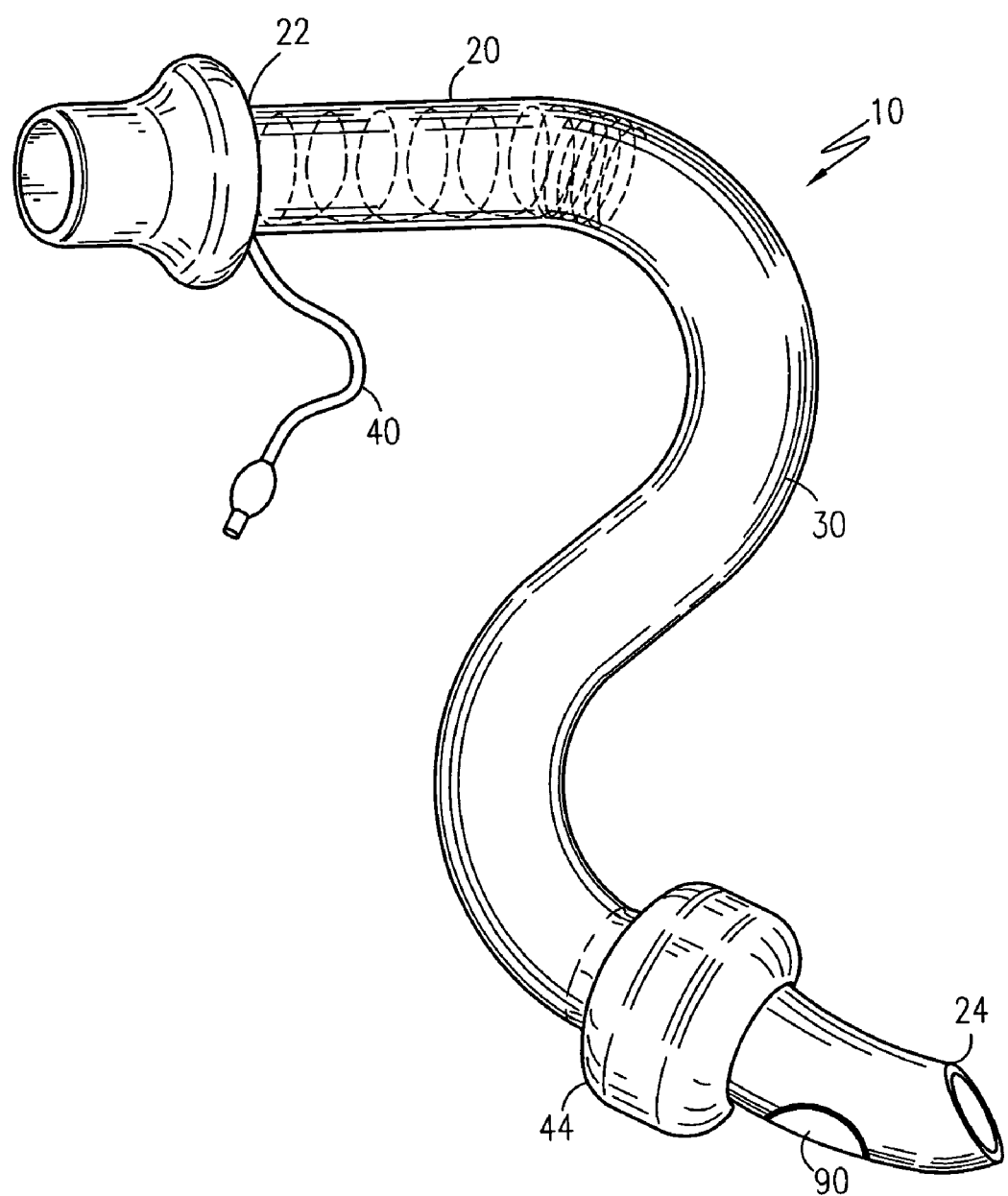
FIG. 1 is a perspective view of an improved endotracheal tube according to the preferred embodiment of the present invention.

Referring now to FIGS. 1-4, an improved endotracheal tube 10 is shown, according to the present invention, comprised of an endotracheal tube 20 having an elongated body 30 with a cephalic end 22 and a caudal end 24. The endotracheal tube 20 is constructed of a sufficiently flexible, latex-free transparent material adapted to flexibly and safely accommodate anatomically the nasopharyngeal airway during the process of nasopharyngeal intubation.

An inflation tube 40 joins body 30, wherein inflation tube 40 functions as a conduit for introducing air or fluid at either high or low pressures to inflate a cuff 44. Inflation tube 40 and cuff 44 will be described later in greater detail.

The novelty of applicant's endotracheal tube 20 lies in a nasopharyngeal section 25 defined at the cephalic end 22 and extending downward therefrom a longitudinal length which incorporates a spirally-wound coil 50.

Figure 2:
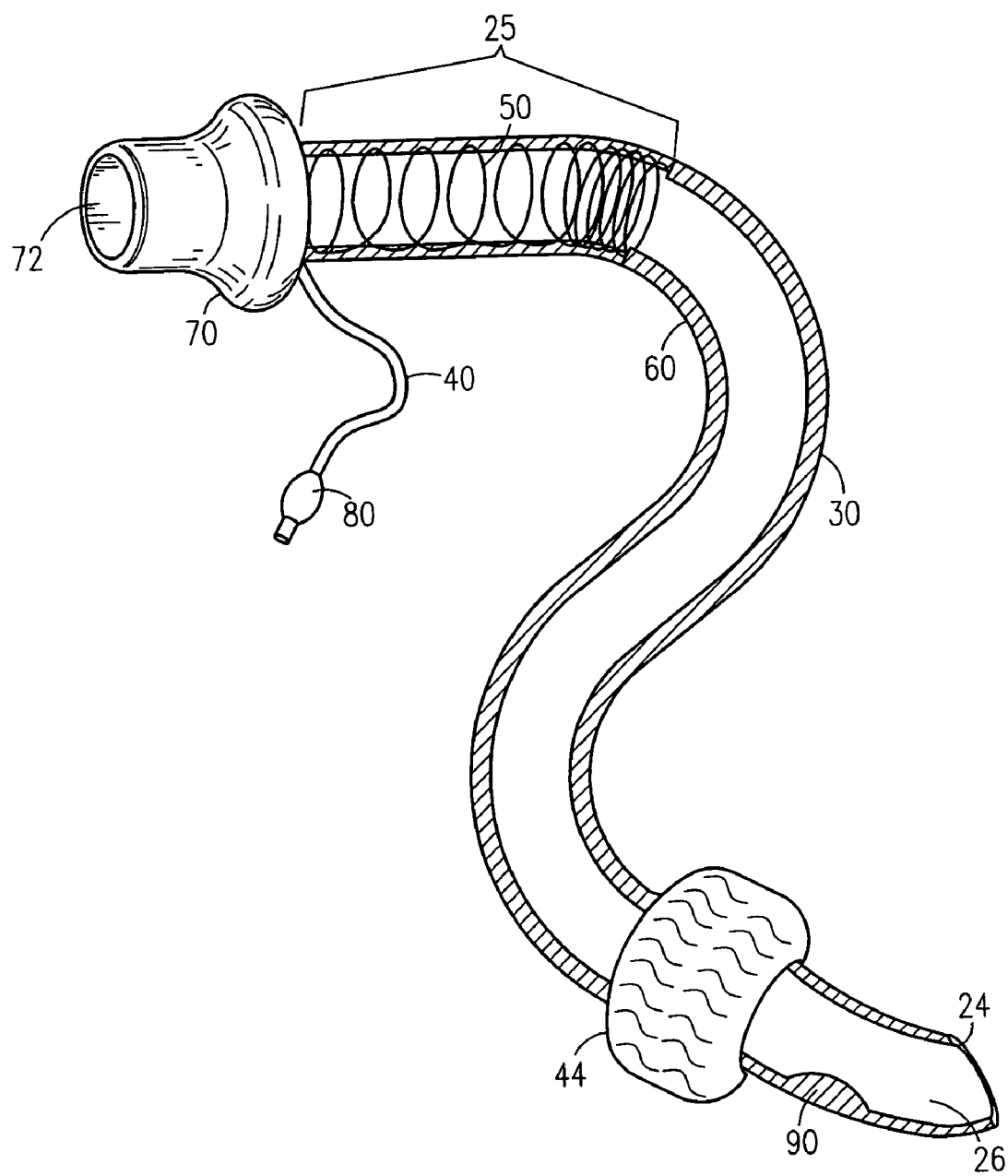
FIG. 2 is a partial cross-sectional view thereof.
Figure 3:
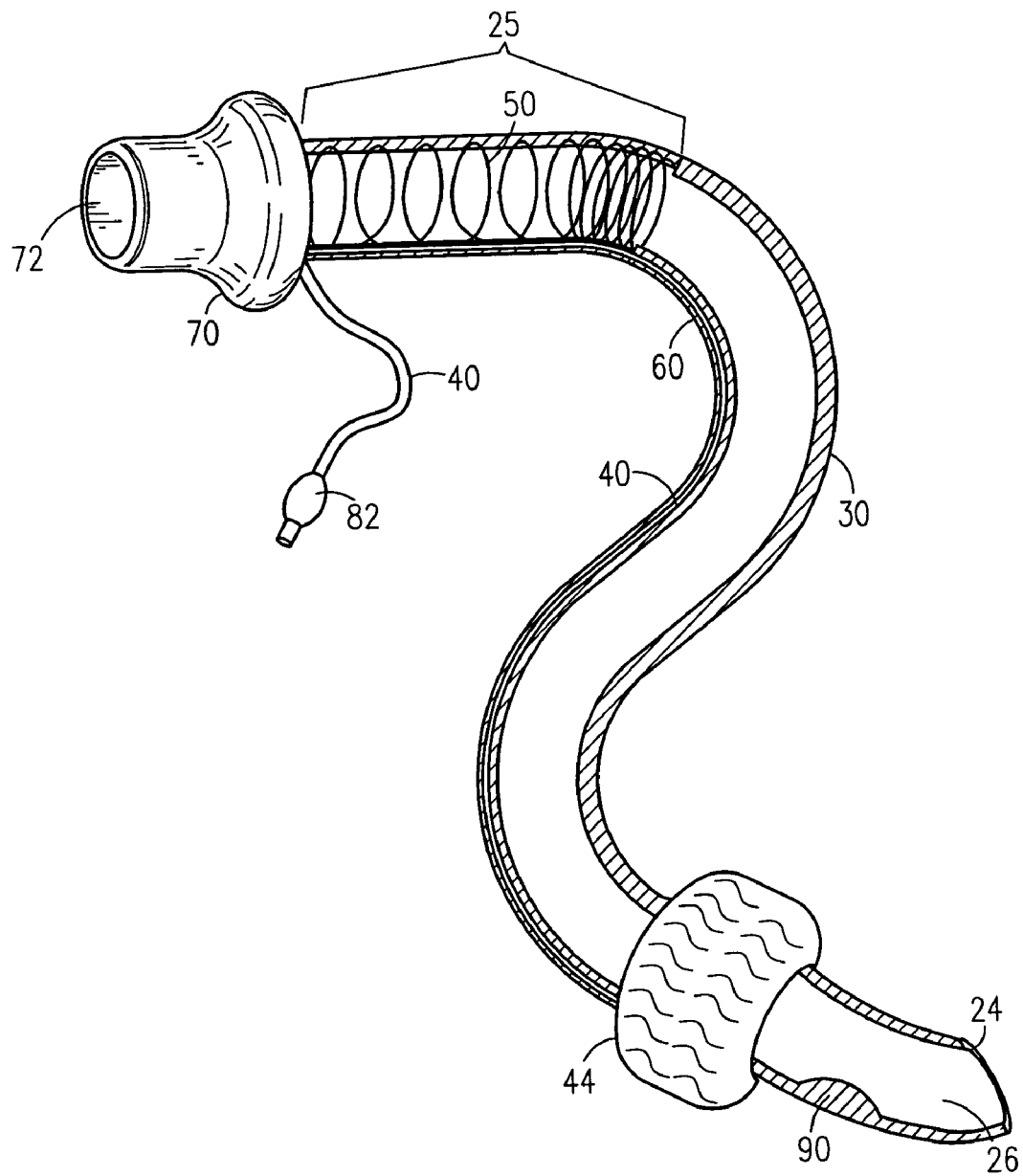
FIG. 3 is a partial cross-sectional view of the present invention according to the preferred embodiment.

Referring more specifically to FIGS. 2 & 3, the nasopharyngeal section 25 is further defined as a thin-wall section constructed of a flexible, latex-free transparent material adapted to flexibly accommodate the anatomy of the nasopharyngeal airway, and further being sufficiently pliable so as to be compressed and adapted to resume its original shape. It is envisioned that the nasopharyngeal section 25 is formed of a flexible, latex-free plastic polymer selected from the group consisting of thermosensitive siliconized polyvinyl chloride, polyurethane, polyethylene, and polyethylene terephthalate. The nasopharyngeal section 25 is further adapted to sealably enclose and contain the spirally-wound coil 50 longitudinally therealong. FIGS. 2 & 3 clearly Illustrate the spirally-wound coil 50 embedded within the nasopharyngeal section 25 of tube 20.

The spirally-wound coil 50 is fabricated of a shape-memory, flexible material is partially compressed within the distal end of the nasopharyngeal section, and is further adapted to return to or recover its original shape if additionally compressed. While capable of being made of a metallic or metallic-plastic composite, in the preferred embodiment the coil 50 would be consistent with the nasopharyngeal section 25, the spirally-wound coil 50 is constructed of a flexible material adapted to flexibly accommodate the anatomy of the nasopharyngeal airway. The spirally-wound coil 50 is envisioned to be formed of a flexible, pliable plastic polymer selected from the group consisting of silicone rubber, polyethylene, polyurethane, and polyethylene terephthalate.

The thin-wall section or nasopharyngeal section 25 integrally transposes into a rigid section 60 which extends longitudinally therefrom and terminates at the caudal end 24. While the nasopharyngeal section integrally transposes to the rigid section about a smooth external surface, the internal diameter of the nasopharyngeal section is different than the internal diameter of the rigid section. In this manner, accommodation can be made for receiving the spirally-wound coil in a manner that allows the formation of a shape-memory, flexible material that allows said nasopharyngeal section to remain in a selected position, while at the same time preventing obstruction to fluid flow within the tube. The caudal end 24 defines an opening 26 adapted to allow for flow of air or gas therethrough. The length of the rigid section 60 is of a longitudinal measure adapted to accommodate proper airway depth so as to ensure intubation is in conformance with that which is adopted and recognized in the medical arts.

The rigid section 60 is formed of a flexibly-rigid material adapted to facilitate intubation through both the nasopharyngeal and oral airways without impedance or undue hindrance. It is envisioned that rigid section 60 is constructed of a semi-rigid or rigid polymeric plastic, latex-free material selected from the group consisting of thermosensitive polyvinyl chloride, polyurethane, and polyethylene.

The length of the nasopharyngeal section 25 is of a longitudinal measure adapted to accommodate proper nasopharyngeal airway depth as is adapted for use and recognized in the art. The fabrication materials utilized for forming the nasopharyngeal section 25 and the embedded spirally-wound coil 50, in conjunction with their respective longitudinal lengths, provide for unique advantages. More specifically, the nasopharyngeal section 25 with incorporated spirally-wound coil 50 facilitates multiple positioning thereof about a face of a patient, thereby minimizing pressure sores, abrasions, and ulcerations. In addition, the pliable, flexible construction of the nasopharyngeal section 25 and spirally-wound coil 50 allows for quick, easy, and efficient surgical access to the nasopharyngeal airway without requiring removal of the endotracheal tube 20.

Figure 4:
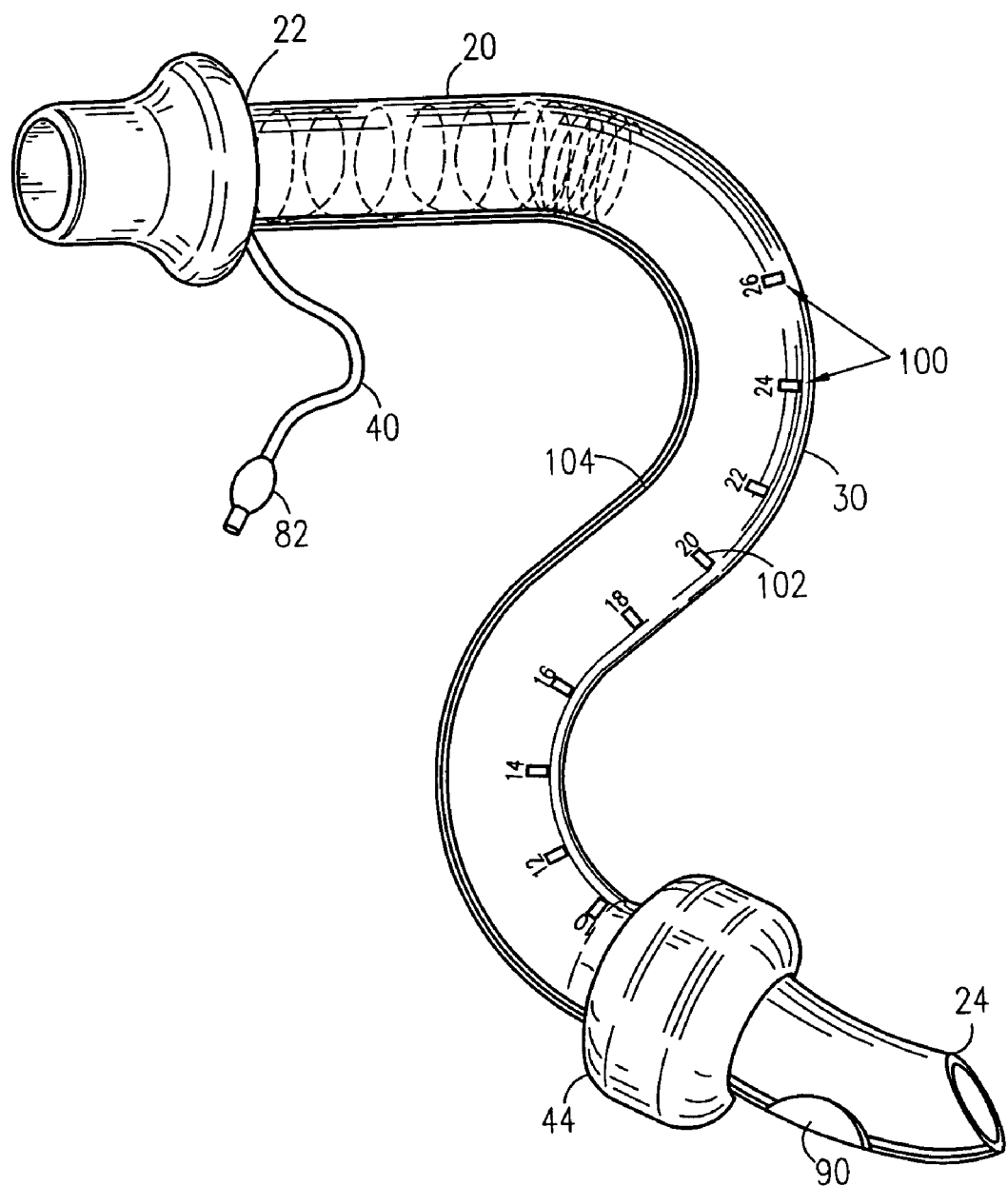
FIG. 4 is a perspective view of the present invention illustrating the plurality of indicia according to the preferred embodiment.

Referring now to FIGS. 3 & 4, the cephalic end 22 of endotracheal tube 20 is provided with an outer end fixture 70 having an open end 72 for providing passage into endotracheal tube 20.

The inflation tube 40 is inserted through and is embedded within an inner sidewall of body 30 at cephalic end 22, from which inflation tube 40 extends longitudinally therefrom and connects to cuff 44, to which inflation tube 40 is in fluid/air communication. Inflation tube 40 is sealably retained within inner sidewall of body 30. The cuff 44 is inflated by passing air or fluid at high or low pressures via an inflation mechanism 80, shown herein as a pilot balloon 82.

An auxiliary opening 90 or "Murphy Eye" opening is defined through an outer sidewall of endotracheal tube 20 being proximal to the caudal end 24 thereof. Cuff 44 is positioned above auxiliary opening 90. The auxiliary opening 90 is adapted to provide an alternate ventilation port should the caudal end 24 of endotracheal tube 20 becomes occluded.

Finally, referring to FIG. 4, a plurality of indicia 100 is provided on an outer surface of endotracheal tube 20. The plurality of indicia 100 is defined longitudinally about endotracheal tube 20 and displays markings which reflect length measures 102 corresponding to endotracheal tube's 20 length. The plurality of indicia 100 further includes a radio opaque marking 104 to allow for x-ray evaluation.

2. Operation of the Preferred Embodiment

To use the present invention, user inserts the caudal end 24 of endotracheal tube 20 through patient's nasal airway to a proper depth while allowing the cephalic end 22 thereof to protrude outwardly from nasal cavity, and thereby allowing the flexible nasopharyngeal section 25 to be manipulated by medical care specialists as needed.

The use of the present invention minimizes pressure sores, abrasions, and ulcerations, and further allows for surgical access to the nasopharyngeal airway without requiring removal of the endotracheal tube in a manner which is quick, easy, and efficient.

Therefore, the foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be broadly limited only by the following Claims.

What is claimed is:

1. An endotracheal tube comprising: a nasopharyngeal section;
   a rigid section;
   an opening defined at the terminal end of said rigid section adapted to allow for flow of air or gas therethrough;
   an inflation tube, wherein said inflation robe functions as a conduit for introducing air or fluid at either high or low pressures to inflate a cuff;
   a spirally-wound coil enclosed within said nasopharyngeal section, wherein the coil is partially compressed within the distal end of the nasopharyngeal section; and,
   an outer end fixture, said outer end fixture being attached to said nasopharyngeal section of said endotracheal tube, said outer end fixture having an open end for providing passage into said endotracheal tube,
   wherein said nasopharyngeal section and said rigid section form a single, elongated body of continuous length and having a constant external diameter wherein said nasopharyngeal section integrally transposes to said rigid section about an external surface, wherein the internal diameter of said nasopharyngeal section is different than the internal diameter of said rigid section and wherein said spirally-wound coil is fabricated of a shape-memory, flexible material that allows said nasopharyngeal section to remain in a selected position.

2. The endotracheal tube of claim 1, wherein said spirally wound coil is adapted accommodate a nasopharyngeal airway during a process of nasopharyngeal intubation.

3. The endotracheal tube of claim 1, wherein said nasopharyngeal section is further defined as a thin-wall section constructed of a flexible, latex-free transparent material adapted to flexibly accommodate an anatomy of a nasopharyngeal airway, and further being sufficiently pliable so as to be compressed and adapted to resume its original shape.

4. The endotracheal tube of claim 1, wherein said nasopharyngeal section is adapted to sealably enclose and contain longitudinally said spirally-wound coil.

5. The endotracheal tube of claim 1, wherein said nasopharyngeal section is formed of a flexible, latex-free plastic polymer.

6. The endotracheal tube of claim 5, wherein said flexible, latex-free plastic polymer is selected from the group consisting of thermosensitive siliconized polyvinyl chloride, polyurethane, polyethylene, and polyethylene terephthalate.

7. The endotracheal tube of claim 1, wherein said spirally-wound coil is formed of a material selected from the group comprising:
   a flexible material;
   a pliable plastic polymer;
   a metal; and
   a metal-polymer composite.

8. The endotracheal tube of claim 7, wherein said flexible, pliable plastic polymer is selected from the group consisting of silicone rubber, polyethylene, polyurethane, and polyethylene terephthalate.

9. The endotracheal tube of claim 1, wherein said rigid section defines a length having a longitudinal measure adapted to accommodate proper airway depth so as to ensure intubation is in conformance with that which is adopted and recognized in medical arts.

10. The endotracheal tube of claim 9, wherein said rigid section is formed of a flexibly-rigid material adapted to facilitate intubation through a nasopharyngeal and an oral airway without impedance or undue hindrance.

11. The endotracheal tube of claim 10, wherein said rigid section rigid section is constructed of a semi-rigid or rigid polymeric plastic, latex-free material.

12. The endotracheal tube of claim 1, wherein said inflation tube is inserted through and is embedded within an inner sidewall of said nasopharyngeal section and said rigid section, from which said inflation tube extends longitudinally and connects to said cuff, said inflation tube is in fluid/air communication with said cuff, said inflation tube is sealably retained within said inner sidewall of said nasopharyngeal section and said rigid section, and wherein said cuff is inflated by passing air or fluid at high or low pressures via an inflation mechanism.

13. The endotracheal tube of claim 1, wherein said body of said endotracheal tube includes an auxiliary opening defined through an outer sidewall of said body, said auxiliary opening is located proximal to said rigid section, said cuff is positioned above said auxiliary opening, and wherein said auxiliary opening is adapted to provide an alternate ventilation port should said rigid section becomes occluded.

14. The endotracheal tube of claim 1, wherein said body is provided with a plurality of indicia disposed atop an outer surface of said nasopharyngeal section and said rigid section.

15. The endotracheal tube of claim 14, wherein said plurality of indicia is defined longitudinally about said nasopharyngeal section and said rigid section, said plurality of indicia comprises markings which reflect length measures corresponding to a length of said nasopharyngeal section and said rigid section.

16. The endotracheal tube of claim 14, wherein said plurality of indicia further comprises a radio opaque marking adapted to allow for x-ray evaluation.

17. The endotracheal tube of claim 1, wherein said nasopharyngeal section with incorporated said spirally-wound coil are conjunctively configured and formed of materials adapted to facilitate multiple positioning about a face of a patient during intubation, thereby minimizing pressure sores, abrasions, and ulcerations, and further allows for quick, easy, and efficient surgical access to the nasopharyngeal airway without requiring removal of said endotracheal tube.

* * * * *